US011353387B2

(12) United States Patent
Allouche et al.

(10) Patent No.: US 11,353,387 B2
(45) Date of Patent: Jun. 7, 2022

(54) DETERMINING MULTI-PHASIC FLUID PROPERTIES AND HYDROCARBON PRODUCTION INFORMATION AS A FUNCTION THEREOF (71) Applicant: Schlumberger Technology Corporation, Sugar Land, TX (US)

(72) Inventors: Francis Dominique Allouche, Clamart (FR); Mathilde Jan, Paris (FR)

(73) Assignee: Schlumberger Technology Corporation, Sugar Land, TX (US)

(*) Notice: Subject to any disclaimer, the term of this patent is extended or adjusted under 35 U.S.C. 154(b) by 570 days.

(21) Appl. No.: 16/311,047

(22) PCT Filed: Jun. 21, 2017

(86) PCT No.: PCT/US2017/038411
§ 371 (c)(1),
(2) Date: Dec. 18, 2018

(87) PCT Pub. No.: WO2018/005173
PCT Pub. Date: Jan. 4, 2018

(65) Prior Publication Data
US 2019/0323936 A1 Oct. 24, 2019

(30) Foreign Application Priority Data

Jun. 29, 2016 (EP) .................................... 16290120
Jun. 29, 2016 (EP) .................................... 16290121

(51) Int. Cl.
*G01N 13/00* (2006.01)
*G01B 15/02* (2006.01)
(Continued)

(52) U.S. Cl.
CPC ............. *G01N 13/00* (2013.01); *G01B 15/02* (2013.01); *G01N 22/00* (2013.01); *G01N 33/2847* (2013.01); *G01N 2013/003* (2013.01)

(58) Field of Classification Search
CPC .... G01N 13/00; G01N 22/00; G01N 33/2847; G01N 2013/003; G01B 15/02
(Continued)

(56) References Cited

U.S. PATENT DOCUMENTS 4,320,659 A 3/1982 Lynnworth et al.
4,405,988 A 9/1983 Forster et al.
(Continued)

FOREIGN PATENT DOCUMENTS

CA 2267900 A1 4/1998
CN 101858771 A 10/2010
(Continued)

OTHER PUBLICATIONS

Magnetrol; "Level and Flow Solutions for Liquid Gravity Separator Skids"; Pub. Date Mar. 29, 2016; Published by Magnetrol) (Year: 2016).*
(Continued)

*Primary Examiner* — Judy Nguyen
*Assistant Examiner* — Rahul Maini
(74) *Attorney, Agent, or Firm* — Rodney Warfford (57) ABSTRACT A method of determining properties of a fluid having an oil phase, a water phase, and an emulsion phase between the oil phase and water phase includes emitting an electromagnetic wave into the fluid, measuring an amplitude of a reflection of the electromagnetic wave off an interface between the oil phase in order to determine a height of a coalescing portion of the oil/emulsion interface. A height of a creaming portion of the emulsion/water interface is then determined using the coalescing portion height, total fluid height and water-in-
(Continued)

liquid ratio. A thickness of the emulsion phase is determined based on the difference between coalescing and creaming portion height.

19 Claims, 8 Drawing Sheets

(51) Int. Cl.
*G01N 22/00* (2006.01)
*G01N 33/28* (2006.01)

(58) Field of Classification Search
USPC .......................................................... 324/643
See application file for complete search history.

(56) References Cited

U.S. PATENT DOCUMENTS

| | | | |
|---|---|---|---|
| 4,685,522 A * | 8/1987 | Dixon | E21B 43/00 137/624.2 |
| 4,901,245 A | 2/1990 | Olson et al. | |
| 5,203,335 A | 4/1993 | Noujaim et al. | |
| 5,473,934 A | 12/1995 | Cobb | |
| 5,760,297 A | 6/1998 | Weerstra | |
| 5,811,677 A | 9/1998 | Cournane | |
| 6,029,116 A | 2/2000 | Wright et al. | |
| 7,049,831 B2 | 5/2006 | Wooton et al. | |
| 7,078,910 B2 | 7/2006 | Hirthe et al. | |
| 7,621,181 B2 | 11/2009 | Cammarata et al. | |
| 9,476,755 B2 | 10/2016 | Hurmuzlu et al. | |
| 2005/0018176 A1* | 1/2005 | Smith | G01N 33/2823 356/128 |
| 2006/0211128 A1 | 9/2006 | Johnson et al. | |
| 2008/0237141 A1 | 10/2008 | Kerfoot | |
| 2009/0025460 A1 | 1/2009 | Hurmuzlu et al. | |
| 2010/0257931 A1 | 10/2010 | Partington et al. | |
| 2010/0268487 A1 | 10/2010 | Hurmuzlu et al. | |
| 2010/0274503 A1 | 10/2010 | Hurmuzlu et al. | |
| 2012/0123302 A1 | 5/2012 | Liu et al. | |
| 2012/0210768 A1 | 8/2012 | Hurmuzlu et al. | |
| 2012/0285896 A1 | 11/2012 | Black | |
| 2014/0085133 A1 | 3/2014 | Flasza et al. | |
| 2014/0090451 A1 | 4/2014 | Surman et al. | |
| 2014/0090454 A1 | 4/2014 | Surman et al. | |
| 2014/0238679 A1* | 8/2014 | Pope | C10L 1/328 166/300 |
| 2014/0305194 A1 | 10/2014 | Surman et al. | |
| 2015/0084809 A1* | 3/2015 | Flasza | G01F 23/284 342/124 |
| 2016/0129371 A1 | 5/2016 | Black | |
| 2016/0169839 A1 | 6/2016 | Gottlieb et al. | |

FOREIGN PATENT DOCUMENTS

| | | |
|---|---|---|
| EP | 1593418 A1 | 11/2005 |
| EP | 2453230 A1 | 5/2012 |
| EP | 2455727 A1 | 5/2012 |
| EP | 2520909 A1 | 11/2012 |
| GB | 2501165 A | 10/2013 |
| JP | H0510899 A | 1/1993 |
| WO | 2009063194 A2 | 5/2009 |

OTHER PUBLICATIONS

Meribout et al., Interface Layers Detection in Oil Field Tanks: A Critical View (29 pages).
Thomenius, Evolution of Ultrasound Beamformers, 1996 IEEE Ultrasonics Symposium (8 pages).
Von Ramm et al., Beam Steering with Linear Arrays, Aug. 1983 (15 pages).
Kinsler and Frey, Reflection and Transmission; Fundamentals of Acoustics, 2000, chapter 6 (16 pages).
International Search Report and Written Opinion issued in the related PCT application PCT/US2015/046211 (032299-WO-PCT), dated Mar. 1, 2016 (21 pages).
International Preliminary Report on Patentability issued in the related PCT application PCT/US2015/046211 (032299-WO-PCT), dated Jun. 13, 2017(16 pages).
Communiation pursuant to Article 94(3) issued in related EP Application 15762837.1 (032299-EP-PCT) dated Aug. 9, 2018 (11 pages).
Search Report and Written Opinion issued in the related SG application 11201704794Y (032299-SG-PCT) dated Apr. 5, 2018 (12 pages).
Search Report and Written Opinion issued in the related SG application 11201704794Y (032299-SG-PCT) dated Mar. 5, 2019 (5 pages).
Extended Search Report issued in the related EP Application 16290120.1 dated Dec. 19, 2016 (11 pages).
Kerbs et al., Separation Kinetics of an oil-in-water emulsion under enhanced gravity, Chemical Engineering Science, vol. 71, Mar. 2012, pp. 118-125.
Skeie et al., Level Estimation in oil/water separators based on multiple pressure sensors and multivariate calibration, Journal of Chemometrics, vol. 24, No. 7-8, Feb. 1, 2010, pp. 387-298.
International Search Report and Written Opinion issued in the related PCT Application PCT/US2017/038411, dated Sep. 18, 2017 (20 pages).
International Preliminary Report on Patentability issued in the related PCT Application PCT/US2017/038411, dated Jan. 10, 2019 (30 pages).

* cited by examiner

DETERMINING MULTI-PHASIC FLUID PROPERTIES AND HYDROCARBON PRODUCTION INFORMATION AS A FUNCTION THEREOF

BACKGROUND

Field

This application claims priority to and the benefit of a EP Application 16290120.1 filed on 29 Jun. 2016 and 16290121.9 filed on 29 Jun. 2016, which are incorporated by reference herein.

This disclosure relates to the field of fluid property determination, and, more particularly, to the determination of properties of a multi-phase fluid, interface phases of a multi-phase fluid, such as an emulsion phase of a multi-phase fluid, and the use of those determined properties for well testing and production well site design and operation.

Description of the Related Art

In oil production, transport, processing, and storage, multi-phase fluids are present. For example, a well may produce multiphase fluid having, for example, a gas phase, a water phase, and an oil phase. Some multiphase fluids may also have a solid phase including sand, mud, or other solid components. Although oil and water are immiscible, at the interface between the water phase and the oil phase an emulsion may form. That is, there may be a phase comprised of a mixture of water droplets in oil, water and oil droplets, and oil droplets and water. Other interface phases may also be present in a multiphase fluid, such as between the oil and gas phase or even between a solid phase and any of the multiphase fluids.

The determination of properties of the emulsion or any of the interface phases may be useful for a variety of reasons relating to storage, transport, or separation of the phases. Current techniques and technologies, however, may not provide for accurate determination of such properties. To that end, further development, both of technologies to accurately determine these properties, as well as new ways of using such accurately determined properties, is desirable.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Disclosed herein is a method of determining properties of a fluid having an oil phase, a water phase, and an emulsion phase between the oil phase and water phase. The method includes emitting an electromagnetic wave into the fluid, and measuring an amplitude of a reflection of the electromagnetic wave off an interface between the oil phase and the emulsion phase. A dielectric constant of the emulsion phase is determined based on the amplitude of the reflection of the electromagnetic wave from the interface. A water-in-liquid ratio of the emulsion phase is determined based on the dielectric constant. A thickness of the emulsion phase is determined based on the water-in-liquid ratio of the emulsion phase.

Another aspect is directed to an apparatus including a vessel containing a fluid having an oil phase, a water phase, and an emulsion phase between the oil phase and water phase. A guided wave radar is associated with the vessel. A computing device is coupled to the guided wave radar and configured to cause the guided wave radar to emit an electromagnetic wave into the fluid, and measure an amplitude of a reflection of the electromagnetic wave off an interface between the oil phase and the emulsion phase, using the guided wave radar. The computing device is further configured to determine a dielectric constant of the emulsion phase based on the amplitude of the reflection of the electromagnetic wave from the interface, and determine a water-in-liquid ratio of the emulsion phase based on the dielectric constant. The computing device determines a thickness of the emulsion phase based on the water-in-liquid ratio of the emulsion phase.

A further aspect is directed to a method that includes determining at least one property of at least one interface phase between adjacent phases of a multi-phasic fluid during a first operating condition of a production system, and determining the at least one property of the at least one interface phase during a second operating condition of the production system different than the first operating condition. A separation model for the multi-phasic fluid is tuned as a function of a difference in the at least one property resulting from change from the first operating condition to the second operating condition.

Yet another aspect is directed to an apparatus including a vessel containing therein a multi-phasic fluid having at least one interface phase between adjacent phases. At least one sensor is associated with the vessel. A computing device is configured to cooperate with the sensor to estimate a property of the emulsion phase during a first operating condition of a production associated system, and to cooperate with the sensor to estimate the property of the emulsion phase during a second operating condition of the production associated system different than the first operation condition. The computing device determines whether change from the first operating condition to the second operating condition changed the property of the emulsion phase.

Another method aspect is a method including estimating a property of an interface phase of a multi-phasic fluid as a function of an amplitude of a reflection of an electromagnetic wave off an interface between the interface phase and an adjacent phase, and determining parameters for a hydrocarbon production wellsite system that produces the multi-phasic fluid, as a function of the property of the interface phase.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings.

FIG. 3 is a graph showing amplitude of reflected electromagnetic waves vs. which phase of a multi-phase liquid the reflections are from.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

Figure 1:
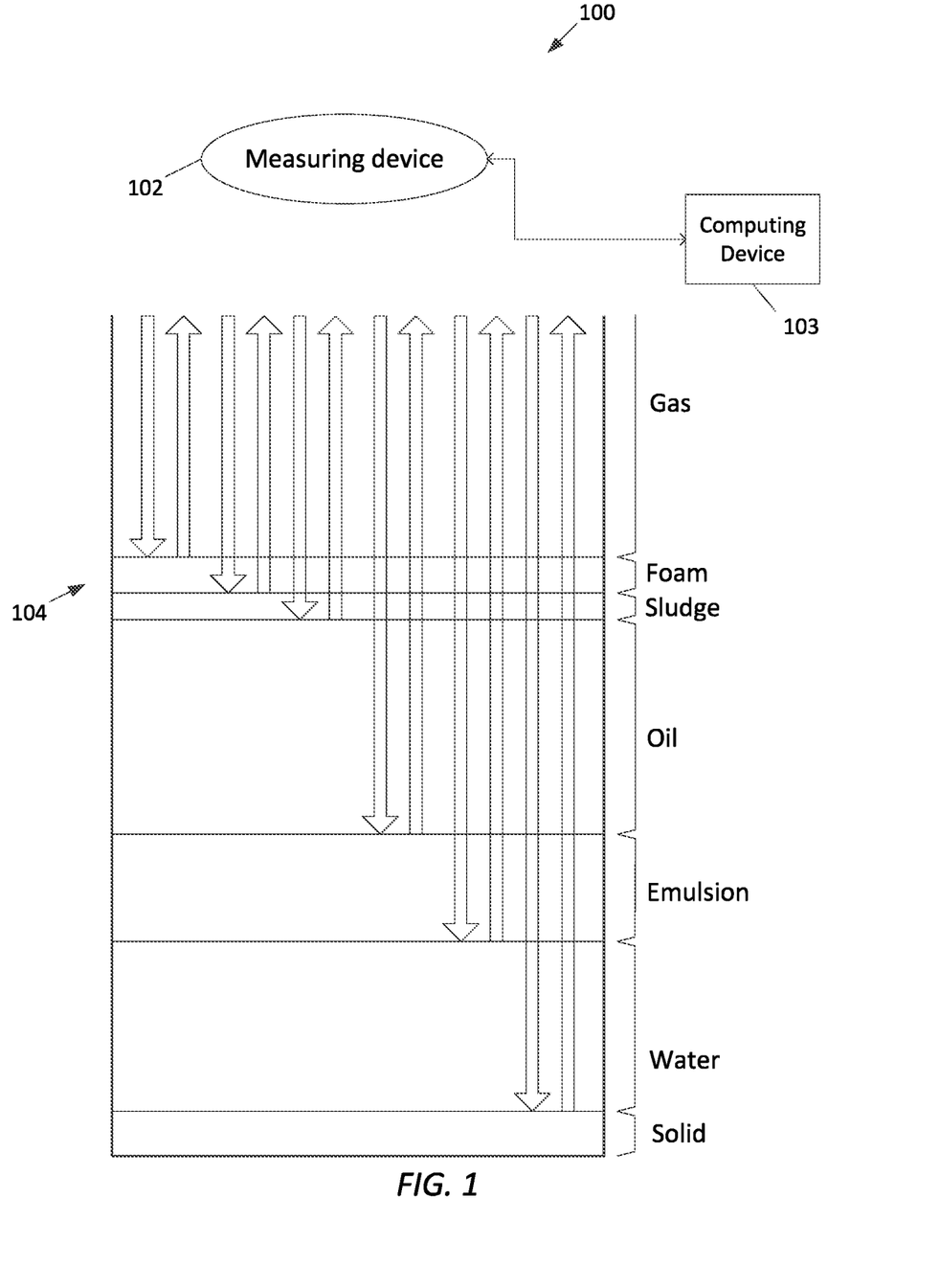
FIG. 1 is a schematic block diagram of a fluid containing vessel and a radar associated therewith, in accordance with this disclosure.

With reference to FIG. 1, a system 100 for determining properties of a fluid is now described. The fluid is contained within a vessel or body 104, which may be a vessel or body of any sort and take any shape. For example, the vessel or body 104 may be a closed tank, closed pipe, production separator, or testing separator.

The fluid has a solid phase, a water phase, an oil phase, an emulsion phase between the water phase and oil phase, a sludge phase, a foam phase, and a gas phase. It should be understood that some of these phases may not be present, and that any combination of these phases may be present. The emulsion phase is heterogeneous, having varying amount of water and oil droplets at different locations.

A measuring device 102 is aimed at the vessel 104, and a computing device 103 is coupled to the measuring device 102 for control thereof and data collection therefrom. The measuring device 102 may be a guided wave radar, for example, although in some applications may be radar, sonar, acoustic, resistivity, gravity, nuclear magnetic resonance, or nuclear measuring device. The measuring device 102 may even include multiple of these types of devices.

The computing device 103 may be a microprocessor, microcontroller, system on a chip, programmed logic controller, field programmable gate array, or other suitable programmable device. It should be appreciated that the computing device 103 has been programmed to perform the functions taught herein, and that such programming causes a change in the physical characteristics of the computing device 103 over a generic unprogrammed computing device. For example, in the case where the computing device 103 is a microprocessor constructed from transistors, the programming changes the biasing of the transistors, which causes physical changes in the semiconductor material of the transistors. In the case where the computing device 103 is a programmed logic controller or field programmable gate array, the programming changes the configuration of the logic gates in the computing device 103.

Example operation will be explained below where the measuring device 102 is a guided wave radar, although as stated above, in some configurations it may not be a guided wave radar. The computing device 103, as will be described below, operates the radar 102 so as to emit electromagnetic waves into the fluid in the vessel 104. The different phases of the fluid each have a different dielectric constant, and thus the amplitude of reflections of the electromagnetic waves off each interface between different phases are different. In addition, by measuring the time elapsed from emission of an electromagnetic wave and receipt of a reflection thereof, the depth or thickness of a phase can be determined.

Figure 2:
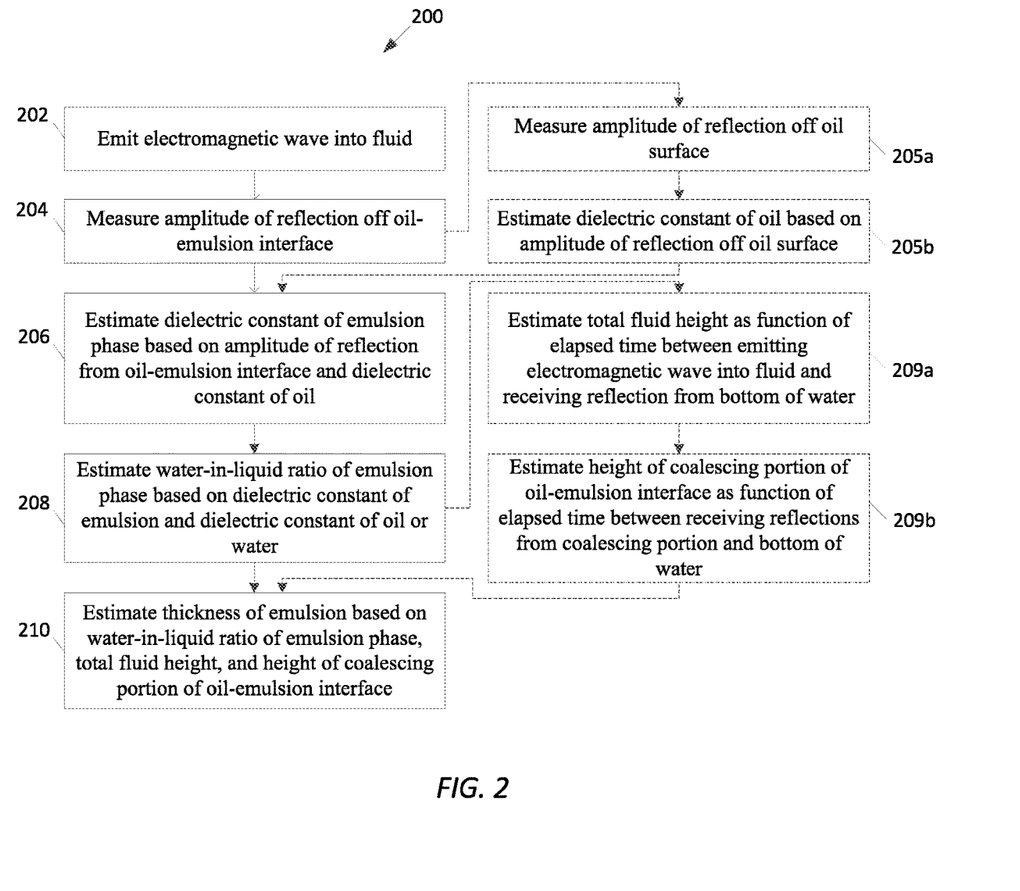
FIG. 2 is a flowchart of a method of determining properties of an emulsion phase of a fluid, such as may be performed with the equipment of FIG. 1, in accordance with this disclosure.
Figure 3:
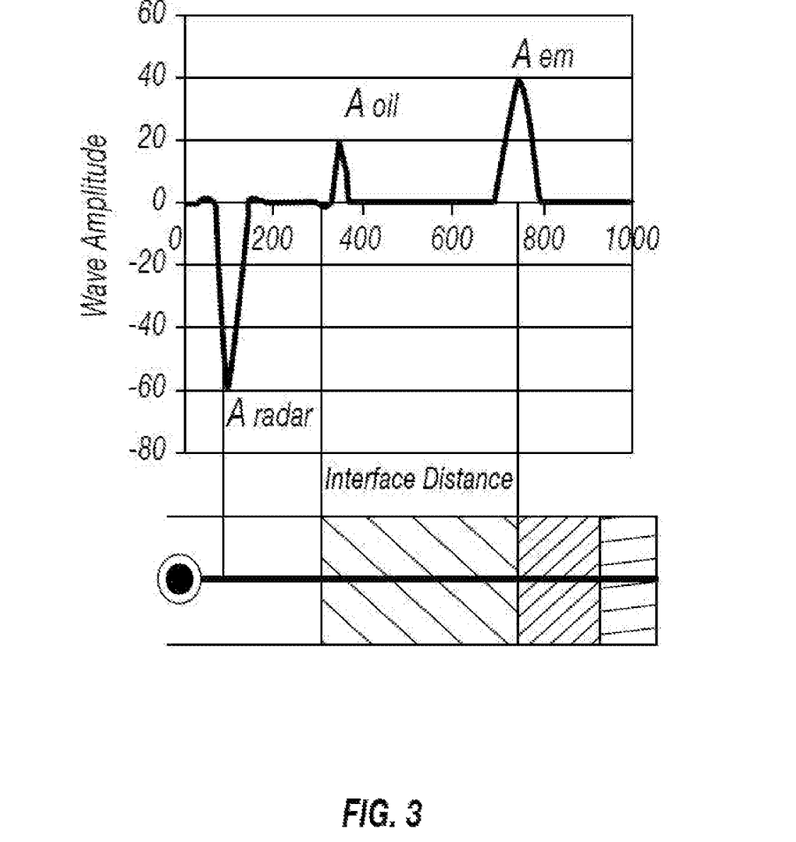

Operation of computing device 103 and radar 102 in order to determine properties of the emulsion phase will now be described with reference to the flowchart 200 of FIG. 2. The technique begins with the computing device 103 operating the radar 102 emit electromagnetic waves into the fluid vessel 104 (Block 202). Then, the computing device 103 measures the amplitude of the reflection of the electromagnetic waves off the interface between the oil phase and the emulsion phase (Block 204). Optionally, if the dielectric constant of the oil is not known, the computing device 103 measures the amplitude of the reflection of the electromagnetic waves off the surface of the oil, which can also be referred to as the interface between the oil and free space (Block 205a). Shown in FIG. 3 is a graph of the amplitude of the reflection from the surface of the oil and from the oil-emulsion interface, which illustrates the difference in amplitudes due to the differences in dielectric constant.

To estimate or determine the dielectric constant of the oil if not already known, the computing device 103, uses the amplitude of the reflection from the surface of the oil to together with the amplitude of the electromagnetic wave as emitted from the radar 102 (Block 205b). Mathematically, the amplitude of the oil is related to the dielectric constant of the oil as follows:

$$A_{oil} = \frac{1 - \sqrt{\varepsilon_{oil}}}{1 + \sqrt{\varepsilon_{oil}}} * A_{radar}$$

where $A_{oil}$ is the amplitude of the reflection from the surface of the oil, $A_{radar}$ is the amplitude of the electromagnetic wave as emitted from the radar, and $\varepsilon_{oil}$ is the dielectric constant of the oil.

Solving for the dielectric constant of the oil thus yields:

$$\varepsilon_{oil} = \frac{\left(\frac{A_{oil}}{A_{radar}} + 1\right)^2}{\left(\frac{A_{oil}}{A_{radar}} - 1\right)^2}$$

The computing device 103 then estimates or determines the dielectric constant of the emulsion phase from the amplitude of the reflection from the oil-emulsion interface and the electric constant of the oil (Block 206). Mathematically, the amplitude of the reflection from the oil-emulsion interface and dielectric constant of the oil are related to the dielectric constant of the emulsion phase as follows:

$$A_{em} = \frac{2}{1+\sqrt{\varepsilon_{oil}}} \frac{\sqrt{\varepsilon_{oil}} - \sqrt{\varepsilon_{em}}}{\sqrt{\varepsilon_{oil}} + \sqrt{\varepsilon_{em}}} \frac{2\sqrt{\varepsilon_{oil}}}{1+\sqrt{\varepsilon_{oil}}} * A_{radar}$$

where $A_{em}$ is the amplitude of the reflection from the oil-emulsion interface, $A_{radar}$ is the amplitude of the electromagnetic wave as emitted from the radar, $\varepsilon_{oil}$ is the dielectric constant of the oil, radar $\varepsilon_{em}$ is the dielectric constant of the emulsion.

Solving for the dielectric constant of the emulsion thus yields:

$$\varepsilon_{em} = \varepsilon_{oil} \frac{(\alpha - \beta)^2}{(\alpha + \beta)}, \text{ where } \beta = \frac{A_{em}}{A_{radar}},$$

$$\text{and where } \alpha = \frac{4\sqrt{\varepsilon_{oil}}}{\left(1+\sqrt{\varepsilon_{oil}}\right)^2}$$

Next, the computing device 103 determines or estimates the water-in-liquid ratio of the emulsion phase based on the dielectric constant of the emulsion and either the dielectric constant of the oil or the dielectric constant of water (Block 208). This correlation may be based on a model. Mathematically, if the dielectric constant of the emulsion and the dielectric constant of oil are used, the relationship is:

$$\varepsilon_{em} = \frac{\varepsilon_{oil}(1 + 2\phi_d)}{1 - \phi_d},$$

where $\phi_d$ is the water-in-liquid ratio

Solving for the water-in-liquid ratio yields:

$$\phi_d = \frac{\varepsilon_m - \varepsilon_{oil}}{\varepsilon_m + 2\varepsilon_{oil}}$$

If the dielectric constant of the emulsion and the dielectric constant of water are used, the relationship is:

$$\varepsilon_{em} = \frac{\varepsilon_{water}(2\phi_d)}{3-\phi_d}$$

Solving for the water-in-liquid ratio yields:

$$\phi_d = \frac{3\varepsilon_{em}}{\varepsilon_{em} + 2\varepsilon_{water}}$$

Figure 4:
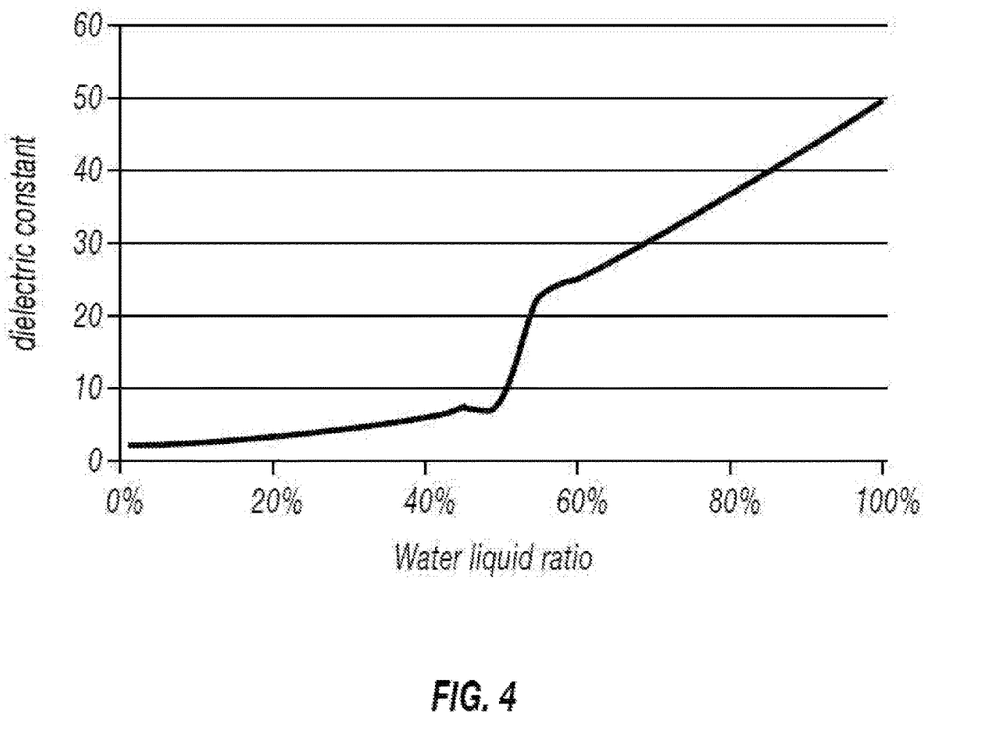
FIG. 4 is an example graph showing the relation between the water liquid ratio and the emulsion phase dielectric constant, for a sample multi-phase liquid.

The relationship between the dielectric constant of an emulsion and a water-in-liquid ratio is shown, for a sample fluid, in FIG. 4. It should be appreciated that the relationship between the dielectric constant of the emulsion and the water-in-liquid ratio, as shown in FIG. 4, may be different for different fluids, depending on the dielectric constant of the oil, the dielectric constant of the water, and the water-in-liquid ratio at which the emulsion is changing from an oil-in-water emulsion to a water-in-oil emulsion.

Optionally, if not yet known, the total fluid height is estimated or determined by the computing device 103 (Block 209a). This is done by measuring the elapsed time between emission of the electromagnetic waves from the radar 102 and receiving a reflection of the electromagnetic waves from the bottom of the water (such as a reflection off the bottom of the vessel 104).

Figure 5:
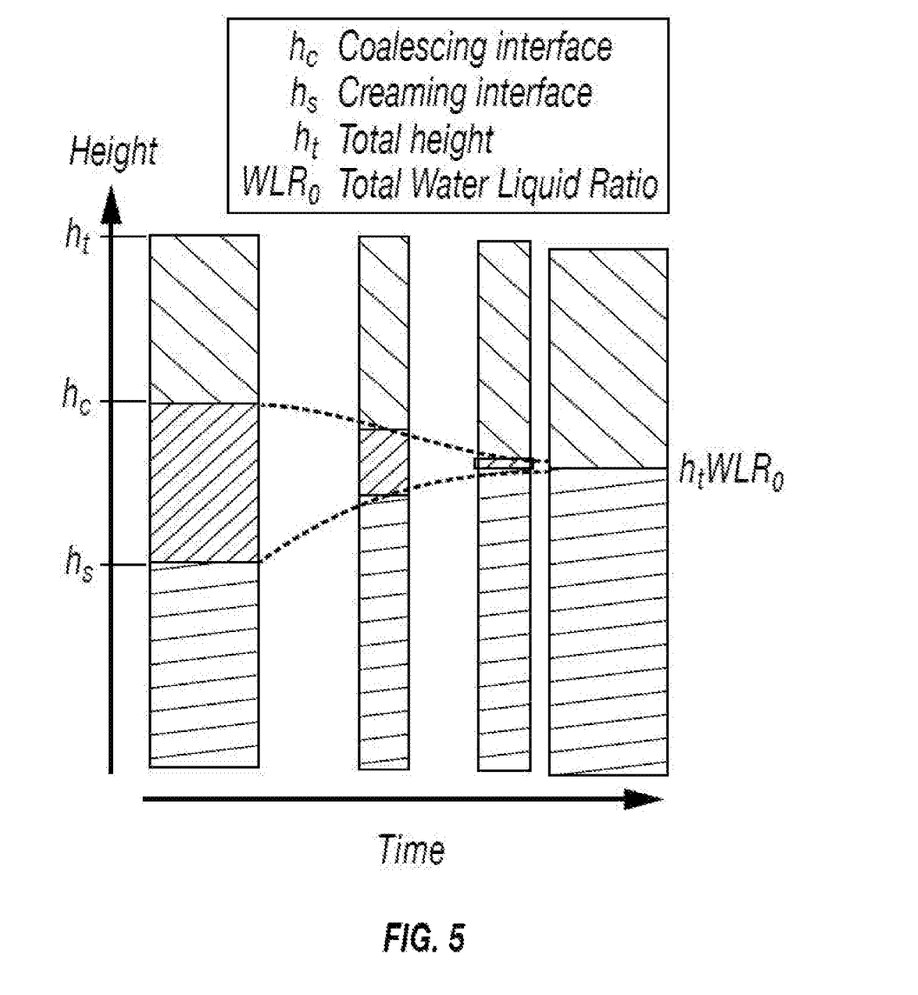
FIG. 5 is a graph showing changes in position of the coalescing portion and the creaming portion of the emulsion phase of a multi-phase liquid over time.

Those of skill in the art will understand that, just as the interface between the oil and water phases is not precise, resulting in the emulsion, the emulsion phase itself is not homogenous but is rather heterogeneous. The upper portion or interface of the emulsion phase where it meets the oil phase is called the coalescing interface, while the lower portion or interface of the emulsion phase where it meets the water phase is called the creaming interface. Over time the height between the coalescing interface and the creaming interface grows smaller, as shown in FIG. 5.

If not already known, the height of the coalescing portion is estimated or determined by the computing device 103 (Block 209b). This is done by measuring the elapsed time between emission of the electromagnetic waves and receiving the reflections from the coalescing portion.

Next, the computing device 103 estimates or determines the thickness of the emulsion phase based on the water-in-liquid ratio of the emulsion phase, the total fluid height, and the height of the coalescing portion of the oil-emulsion interface (Block 210). This estimation may be performed using a mass balance model. Mathematically, first the height of the creaming interface is calculated as:

$$h_s = \frac{WLR_0 * h_t - WLR_{em} * h_c}{1 - WLR_{em}},$$

where $h_s$ is the height of the creaming interface, $h_c$ is the height of the coalsecing interface, $h_t$ is the total fluid height, and $WLR_0$ is the total water liquid ratio.

The thickness of the emulsion phase is then calculated as:

$$\text{Thickness}_{em} = h_c - h_s$$

Figure 6:
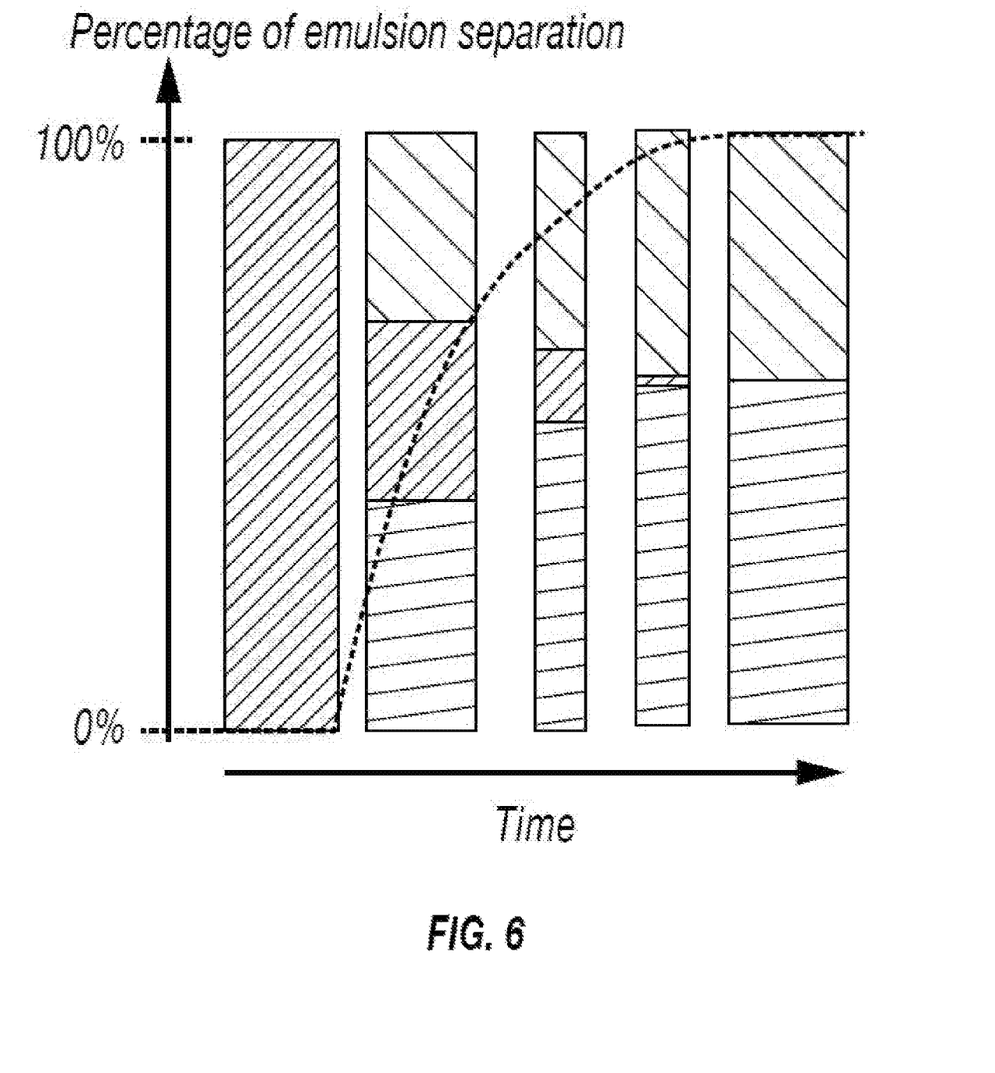
FIG. 6 is a graph showing the percentage of emulsion separation of a multi-phase liquid over time.

The thickness of the emulsion phase is useful in a variety of applications. As shown in FIG. 5, the thickness of the emulsion phase (difference between coalescing interface and creaming interface) subsides over time. This change in emulsion height or thickness over time can be interpreted as a percentage of emulsion separation or subsiding over time (i.e. rate of decrease in thickness over time), as shown in the graph of FIG. 6, allowing for estimation of the percentage of emulsion separation or subsiding over time. These estimations can be referred to as kinetics of separation.

Although the determination of the above characteristics and parameters has been described with reference to the emulsion phase, it should be understood that the techniques described above may be applied in the same way to the determination of those characteristics and parameters for any phase, such as the sludge phase.

In addition, although the determination of these various characteristics and parameters has been described above with respect to the use of a guided wave radar for measuring reflections, it should be appreciated that other techniques may be used to emit a signal into the fluid and measure properties from the various phases and the interfaces between them (including solids or solid phases). The properties of phases of a multiphase fluid (and any solids associated therewith) and interfaces between phases may be measured and determined by using reflection, refraction, and/or absorption techniques, or combinations thereof. The reflection, refraction and/or absorption of signals transmitted to and/or through the phases and interfaces may be measured by using signals all along the electromagnetic energy spectrum to determine the interface and phase properties of the multiphase fluid. The reflection, refraction and/or absorption of signals transmitted to and/or through the phases and interfaces may also be measured by using mechanical signals such as mechanically induced waves, for example sonar, acoustic waves, etc. The phase and interface properties may also be measured and determined by measuring electromagnetic properties of the phases and interfaces therebetween, such as, for example, inductance, conductance, capacitance, resistivity, etc.

Where the measured properties are determined from reflections from various phases and interfaces, similar calculations to those above can be applied to data from any such other technique. Where the measured properties are determined, for example, by signal refraction though the interfaces and/or the various phases, or by signal absorption through the interfaces and/or the various phases, other calculations and techniques may be used to determine the various characteristics and parameters of the fluids discussed above. Similarly, where the measured properties are determined using gamma ray emission or absorption by the interfaces and/or the various phases, neutron emission or absorption by the interfaces and/or the various phases, resistances of the interfaces and/or the various phases, relaxation times of hydrogen atoms of the interfaces and/or the various phases, or forces on the interfaces and/or the various phases due to gravity, other suitable calculations and techniques may be used to determine the various characteristics and parameters of the fluids discussed above. As explained above, some of the other measurement techniques may include radar, sonar, acoustic, resistivity, gravity, optical, nuclear magnetic resonance, and nuclear measurements.

Knowing the thickness of the interface phase, the settling time for the interface phase to subside, the water-in-liquid ratio of the interface phase, a height of a creaming interface of the interface phase, a height of a coalescing interface of the interface phase, and the kinetics of separation, each of which the techniques described above now make possible, is useful in a variety of applications. By kinetics of separation, times for, or rates at which, the interfaces decrease in thickness or subside is meant.

At the early stages of the process of exploring and appraising potential hydrocarbon bearing formations, a variety of information is gathered to verify the economic potential as well as the potential productivity of wells drilled in those potential hydrocarbon bearing formations. In gathering this information, formation fluids are quantitatively and qualitatively characterized, which in turn provides for the basis of the design of production operations to retrieve the hydrocarbons from the formation. The design includes the layout of wells themselves, and the architecture and layout of the surface production system with its interconnecting network of pipelines, production facilities, and export lines.

One major function of the production facilities is to separate the various phases of produced fluids. In order to optimize this separation, a proper and suitable size for the separators utilized over the total estimated production for the life of the formation is to be determined. Criteria utilized in sizing the separating devices is dependent on the type of separation processes being used (the main mechanisms that may be utilized include gravity, electrostatic, electromagnetic, thermal, centrifugal, and distillation).

Each type of separating process uses models to describe the kinetics of the separation between the phases. For example, Stoke's Law may be used to determine what retention times would be effective to achieve a desired degree of separation between a mixture of fluids of different densities, where gravity based separators are used. A useful parameter in this particular model is the size of the droplets of the discontinuous phase (such as the emulsion phase or sludge phase) that are to eventually float on or sink into the continuous phase (such as the water phase or the oil phase). Droplet size, however, is difficult to determine or estimate using conventional techniques.

Other parameters, such as the interfacial tension between the fluids also play a role in the separation model for the kinetics of gravity separators. Indeed, common sizing software for separator devices accepts as input a number of parameters that are either challenging to measure or unknown. Consequently, "rules of thumb," instead of actual data analysis, are applied to perform the design and optimization, and therefore, it is not uncommon for a completed production facility to be found sub optimal once placed into operation. Since the techniques described above for determining the kinetics of separation for interface phases provide for accurate determination of these various parameters, the use of such techniques may provide for enhanced optimization and design of production facilities.

Figure 7:
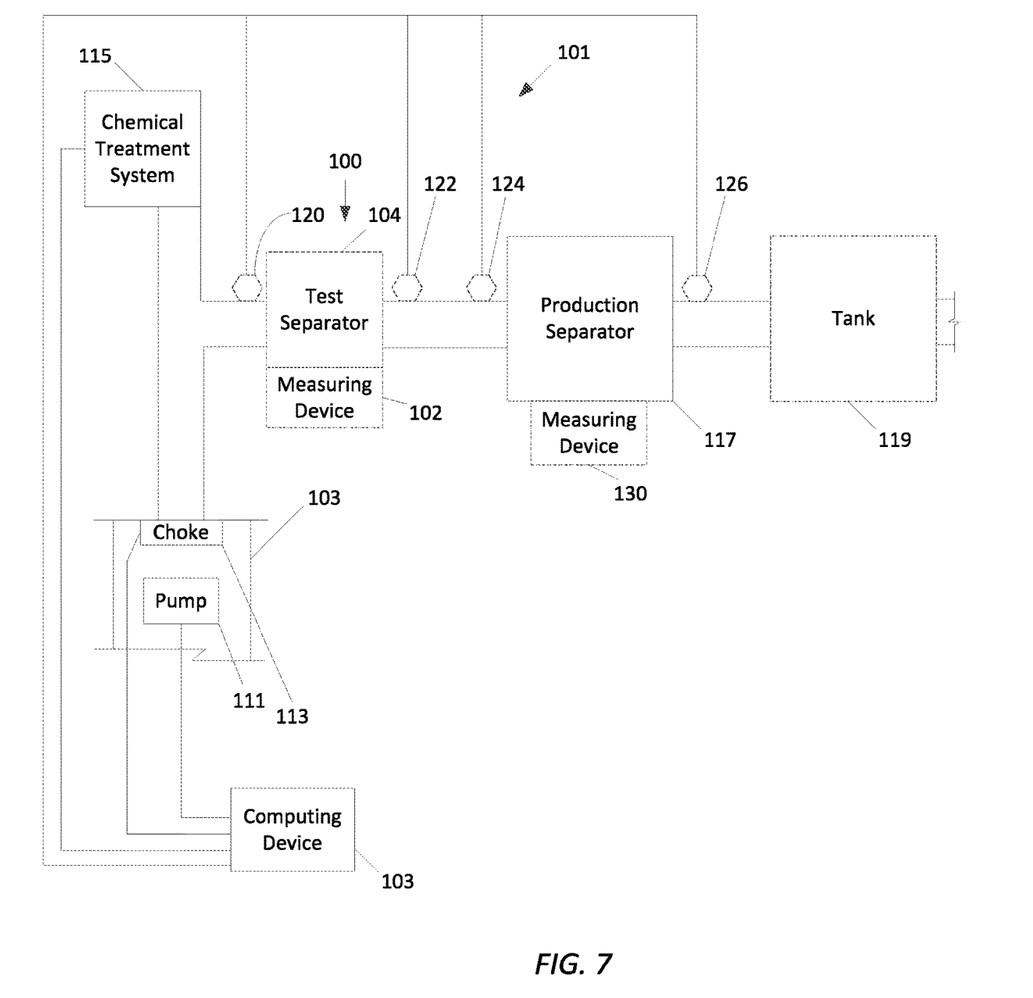
FIG. 7 is a schematic block diagram of a wellsite production system employing the vessel and radar disclosed herein.

With reference to FIG. 7 a system to quantify the separability of multiphase fluids is described. A wellsite production system 101 at which the system 100 is shown. The wellsite production system 101 includes a pump 111 disposed within the wellbore 103 which serves to pump fluid out of the wellbore 103. A well choke 113 serves to help control the flow rate of the fluid from the wellbore. The pump 111 serves to pump the fluid into a production separator 117, which itself serves to separate the various phases of the multi-phasic fluid. A chemical treatment system 115 may chemically treat the fluid as it is pumped into the production separator.

As will be described below, a measuring device 102, such as a guided wave radar or other system used for collecting data about the multi-phasic fluid, phases and/or interface phases thereof, may optionally be located in an optional test separator 104. The optional test separator 104 is plumbed into the wellsite production system 101, is smaller than the production separator 117, and contains a lesser volume of fluid than the production separator 117. In the case where the optional test separator 104 is not used, a measuring device 130 similar to the measuring device 102 above may be used for collecting data about the multi-phasic fluid, phases and/or interface phases thereof, and may be located in the production separator 117.

Other possible measuring devices 102 and 130, other than guided wave radars, usable with the test separator 104 and production separator 117 may be those previously described, including, but not limited to, radar, sonar, acoustic, gravity, optical, inductance, conductance, capacitance, resistivity nuclear magnetic resonance, and nuclear measurement systems.

Optional sensors 120 and 122 may be located at the input and/or output of the optional test separator 104 and coupled to the computing device 103. Similarly, optional sensors 124 and 126 may be located at the input and/or output of the production separator and coupled to the computing device 103. It should be appreciated however that the sensors 120, 122, 124, 126 may be located anywhere useful within the wellsite production system 101.

These sensors 120, 122, 124, and 126 may be sensors used by the computing device 103 to determine the water-in-liquid ratio of the multi-phasic fluid, temperature of the multi-phasic fluid, pressure of the multi-phasic fluid, velocity of the multi-phasic fluid, flow rate of the multi-phasic fluid, or other such properties.

An optional tank 119 is coupled downstream of the production separator 117 and serves to allow for additional subsiding of the interface phase or phases in cases where the interface phase or phases have not subsided completely while in the production separator 117.

Figure 8:
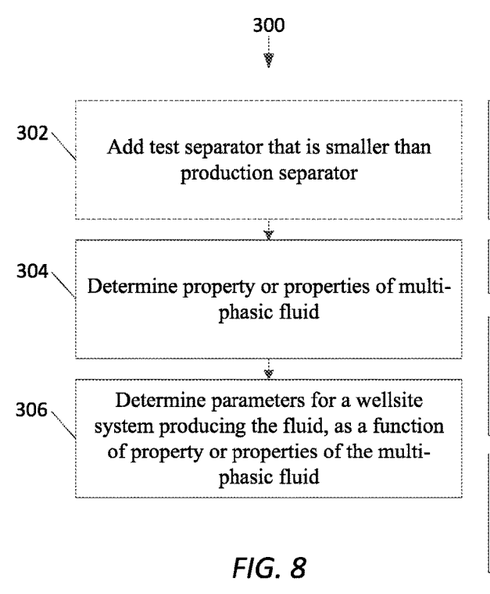
FIG. 8 is a flowchart of a method of using determined properties of an emulsion phase of the fluid.

With reference to the flowchart 300 of FIG. 8, a method of applying information about the multi-phasic fluid, such as the various information about the phases collected above, is now described. As stated, a test separator 104 may optionally be added (Block 302) to the fluid flow. The test separator 104 collects fluid in parallel with the production separator 117. A property or various properties of the multi-phasic fluid is then detected and/or determined or estimated (Block 304), such as by using the measuring device 102 or measuring device 130. As an example, these properties may include the kinetics of separation of the interface phase or phases, the fraction of the multi-phasic fluid represented by each phase, the water-in-liquid ratio of the multi-phasic fluid, the density of the multi-phasic fluid, the resistivity profile of the multi-phasic fluid, the hydrogen index of the multi-phasic fluid, and/or the salinity of the multi-phasic fluid.

As explained above, determination of the various properties of the multi-phasic fluid, phases and/or interface phases thereof may be performed via any suitable method. This determination of the various properties of the multi-phasic fluid, phases and/or interface phases thereof may be performed during continuous flow of the multi-phasic fluid through the test separator 104 or production separator 117, or during a batch settling operation taking place within the test separator 104 or production separator 117. The selection of the mode (continuous or batch) may depend on the kinetics of the process and the model being used.

This determination of the various properties of the multi-phasic fluid, the phases, and/or interface phases thereof may be made on the fluid within a main compartment of the test separator 104 or production separator 117, for example, such as described above in the guided wave radar application. As an alternative, the determination of the various properties of the multi-phasic fluid, the phases, and/or interface phases thereof may be made at an outlet of the production separator 117 using the optional sensor 126, at an inlet of the production separator 117 using an optional sensor 124, at an outlet of the test separator 104, or at an inlet of the test separator 104. For instance, the sensors 120, 122, 124, or 126 may determine the temperature of the multi-phasic fluid, pressure of the multi-phasic fluid, velocity of the multi-phasic fluid, and/or flow rate of the multi-phasic fluid or a phase or interface phase thereof.

In some cases, the determination of the various properties of the multi-phasic fluid, the phases, and/or interface phases thereof may be made as a function of a composition or phase fraction of each phase of the multi-phasic fluid, which may be measured at an outlet of the production separator 117 using the optional sensor 126, at an inlet of the production separator 117 using an optional sensor 124, at an outlet of the test separator 104, or at an inlet of the test separator 104. For example, the sensors 120, 122, 124, and/or 126 may determine the water-in-liquid ratio of the multi-phasic fluid or a phase or interface phase thereof. As another example, one or more of the sensors 120, 122, 124, and/or 126 may be a multiphase flowmeter that uses nuclear technology (x-ray or gamma ray) to determine the fraction of the multi-phasic fluid represented by each phase.

Parameters for the wellsite production system 101 are then determined as a function of the property or properties of the multi-phasic fluid, such as the kinetics of separation of the interface phases (Block 306). These parameters for the wellsite production system 101 may be determined by using a model, and using the determined properties of the multi-phasic fluid as inputs to the model. From the model, or from other tools or processes, a preferred size for the production separator 117 and/or preferred type of internal mechanisms within the production separator 117 may then be determined, for example. Improper sizing of the production separator 117 may increase time used to produce usable hydrocarbons for transport downstream, or may reduce yield due to the emulsion phase not completely subsiding within the production separator 117.

Other determined parameters for the wellsite production system 101 may be a model, size, flow rate, or type of pump 111, a setting for the well choke 113, a pressure, flow rate, or temperature for the fluid, or a chemical treatment regime to be applied by the chemical treatment system 115 to the fluid. Changing the temperature for the fluid may be achieved using a heat exchanger or cooler, well choke, direct heater, or indirect heater.

Also, whether a settling tank 119 is preferred to be added downstream of and in fluid communication with the production separator 117 may be determined. For example, if it is determined that the production separator 117 is not adequately sized to permit the interface phase to subside given current operating conditions, it may be determined that the settling tank 119 is to be added. Also, the duration of time, or settling time, to be spent by the fluid in the settling tank 119 may be one of the parameters determined, as well as whether a sensor to determine a water-in-liquid ratio of fluid is to be installed in the settling tank.

The production separator 117 may be a continuous separator, where oil and water have different velocities and there is thus a continuous feed of emulsion or sludge. Continuous monitoring of the various properties of the multi-phasic fluid may be particularly useful in this case, and alarms may be triggered if the one or more properties takes on an undesirable value. For example, an alarm may be triggered if the multi-phasic fluid, or a phase or interface phase thereof, has a water-in-liquid ratio that is too high for certain purposes, such as burning. Another use for the knowledge of the various properties of the multi-phasic fluid lies in the updating of models used in designing production systems and setups, and even in the design of the models themselves. The models may be of the production systems themselves, or of properties of the production systems. In addition, the various properties of the multi-phasic fluid as determined using the techniques described above may be combined with information about the fluid collected in other fashions, such as by fluid sampling, to create a database, model, or equations which are capable of estimating the kinetics of separation and other properties of the emulsion with simple knowledge of the information collected in the other fashions.

Figure 9:
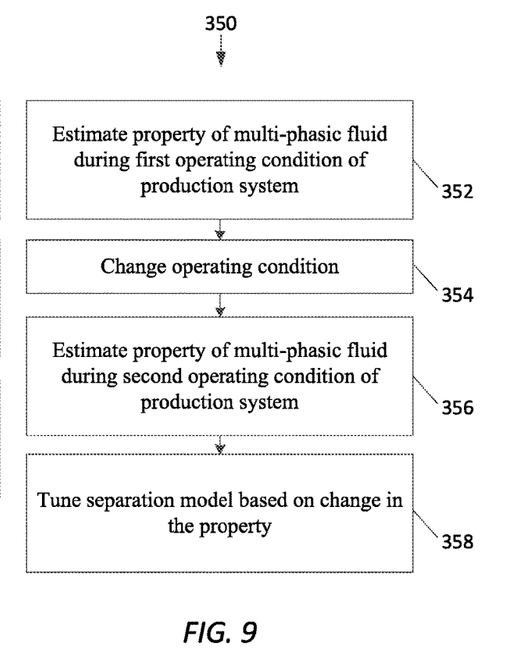
FIG. 9 is a flowchart of another method of using determined properties of an emulsion phase of the fluid.

In some applications, as will now be described with reference to FIG. 9, the various properties of the multi-phasic fluid, such as those of a phase and/or interface phase thereof (i.e. the emulsion phase), are estimated or determined during a first operating condition of the wellsite production system 101 (Block 352). That operating condition is then changed (Block 354) to a second operating condition, and then the various properties of the multi-phasic fluid, such as those of a phase and/or interface phase thereof (i.e. the emulsion phase), are estimated or determined again during the second operating condition (Block 356). The effect of the change from the first operating condition to the second operating condition can then be analyzed, and the separation model may be tuned based thereupon (Block 358), or process control may be changed based thereupon.

Where the production separator 117 operates in continuous separation mode, an example of an operating condition or operating conditions that may be changed are those relative to the production separator 117. In operating in accordance with a first operating condition, the velocity of the multi-phasic fluid through the production separator 117 in continuous separation mode is such that sufficient time for stabilization and separation of the multi-phasic fluid is allowed. As the multi-phasic fluid stabilizes and separates, the transient conditions of the multi-phasic fluid are monitored using the techniques described above to determine the kinetics of separation of one or more phases of the multi-phasic fluid. A steady state analysis (ignoring the transients) on the multi-phasic fluid in the production separator 117 may be used to determine separation efficiency. Conditions of operation of the production separator 117 may then be changed to a second operating condition, for example by changing operating conditions of any component or facet of the wellsite production system 101 as described above or below. Once the conditions of operation of the production separator 117 are changed to the second operating condition, the kinetics of separation and/or separation efficiency may then be determined again. Based on whether the change is considered favorable, the operating conditions of the production separator 117 may be further changed if desired.

Where the production separator 117 operates in batch settling mode, once the production separator 117 is filled to a desired level with the multi-phasic fluid, the multi-phasic fluid is then trapped in the production separator 117 by diverting flowing multi-phasic fluid around the production separator 117. This may be effectuated using suitable combinations of valves and bypass pipes, for example. Once the multi-phasic fluid is trapped, the kinetics of separation and/or separation efficiency are determined as described above. Once the batch settling is complete and the settled multi-phasic fluid has exited from the production separator, one or more operating conditions of the wellsite production system 101 may be changed as described above. A new batch of multi-phasic fluid then flows into the production separator 117, and the trapping function is repeated. Kinetics of separation and/or separation efficiency are then determined as described above. Based on whether the change is considered favorable, the operating conditions of the production separator 117 may be further changed if desired.

The operating condition that is changed may be, for example, mechanical conditions of the wellsite production system 101, such as a control scheme of the pump 111, which may change a flow rate of the pump 111 (i.e. by changing speed), and/or a fluid pressure resulting from operation of the pump 111. Another operating condition that may be changed may be a temperature of the multi-phasic fluid, or a mechanical setting of the choke 113 (i.e. position). That is, the effect of a change in flow rate, pressure, temperature, or choke setting on the multi phasic fluid may be observed and acted upon. The change in flow rate, pressure, temperature, or choke setting may be made at any location within the wellsite production system 101, for example such as by adjusting the pressure of the multi-phasic fluid downstream of the production separator 117, using a flow restrictor or choke. As another example, the pressure of the multi-phasic fluid within the production separator 117 may be adjusted and controlled. Still further, in the case where one or more flow conditioners, such as mixers or strainers, are used within the wellsite production system 101, mechanical conditions of those flow conditioners, such as the shape, position, angle, and size of internal components of the flow conditioners may be adjusted or changed in order to change an operating condition.

The operation condition that is changed may also be a chemical treatment condition of the wellsite production system 101, such as the amounts and/or types of various chemicals injected by the chemical treatment system 115 into the fluid. Sample chemicals include de-emulsifiers, defoamers, and deviscosifiers. By monitoring the properties of the multi phasic fluid, such as those of a phase and/or interphase thereof, between different chemical treatment conditions and comparing the results of the separation efficiencies of the different chemical treatment conditions, it is possible to determine which chemicals, and in what quantities, yield the best separation of the multiphase fluids under a given set of operating conditions. Thus, it may be possible to reduce the amount of such chemicals used while obtaining similar results therefrom, resulting in a cost savings. For example, where an increase of a chemical or chemicals injected during chemical treatment of the multi-phasic fluid does not change a desired property of the multi-phasic fluid, such as kinetics of separation of interface phases, the amount of the chemical or chemicals injected may be reduced.

The operating condition that is changed may also be a volume of one or more of the phases, such that the phase ratio of the makeup of multi-phasic fluid is changed. This may be performed via the use of components of the production separator 117 under control of the computing device 103, such as valves of inlets or outlets at specific fluid levels in the production separator 117. The computing device 103 may control these valves as a function of properties of a phase or interface phase, such as the water-in-liquid ratio or thickness of the emulsion phase. As a result, the residence time of one or more of the phases within the production separator 117 may be changed and controlled. Similar to the change in volume of phases, the volume of the level of multi-phasic fluid in the production separator 117 may be an operating condition that is changed.

Yet another operating condition that may be changed may be the actual equipment of the wellsite production system 101 itself, such as the size or type of the production pump 111. As another example, part of the multi-phasic flow may be diverted from flowing into a desired component, such as the production separator 117. For example, valves may be used to send at least a portion of one or more phases of the multi-phasic fluid through a bypass pipe such that the volume and/or phase ratio of the multi-phasic fluid within the production separator 117 is changed and controlled. In addition to, or instead of, changing a volume of the phases within the production separator 117 or diverting part of the multi-phasic flow through a bypass pipe, additional fluid components such as water or other suitable fluid may be injected into the multi-phasic fluid.

By monitoring the properties of the multi phasic fluid, such as those of a phase and/or interphase thereof, between different operating conditions and comparing the results of the separation efficiencies of the different operating conditions, it is possible to determine which operating conditions yield the best separation of the multiphase fluids.

Although the above has been described with respect to the production separator 117 or test separator 104 utilizing gravity separation, in some applications electrostatic, electromagnetic, thermal, centrifugal, and distillation functionality may be used by the production separator 117 and/or the test separator 104 for separation.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method of determining properties of a fluid having an oil phase, a water phase, and an emulsion phase between the oil phase and water phase, the method comprising:
   emitting an electromagnetic wave into the fluid;
   measuring an amplitude of a reflection of the electromagnetic wave off an interface between the oil phase and the emulsion phase;
   determining a dielectric constant of the emulsion phase based on the amplitude of the reflection of the electromagnetic wave from the interface;
   determining a water-in-liquid ratio of the emulsion phase based on the dielectric constant;
   determining a height of a coalescing portion of the interface between the oil phase and the emulsion phase based on the emitted and reflected waves;
   determining a height of a creaming portion of the interface between the emulsion phase and the water phase based on a difference between a first product and a second product, wherein the first product comprises a product of a total height of the fluid and a total water-in-liquid ratio, and wherein the second product comprises a product of the height of a coalescing portion and the water-in-liquid ratio of the emulsion phase; and
   determining a thickness of the emulsion phase based on the difference between the height of the coalescing portion and the height of the creaming portion.

2. The method of claim 1, wherein the thickness of the emulsion phase is estimated using a mass balance model.

3. The method of claim 1, wherein the dielectric constant of the emulsion phase is determined based on the amplitude of the reflection of the electromagnetic wave from the interface and a dielectric constant of the oil phase.

4. The method of claim 3, further comprising, prior to determining the dielectric constant of the emulsion phase:
   measuring an amplitude of a reflection of the electromagnetic wave off an interface between free space and the oil phase; and
   determining the dielectric constant of the oil phase based on the amplitude of the reflection of the electromagnetic wave off the interface between free space and the oil phase.

5. The method of claim 1, wherein the water-in-liquid ratio of the emulsion phase is determined based on the dielectric constant of the emulsion phase and a dielectric constant of the oil phase.

6. The method of claim 1, wherein the water-in-liquid ratio of the emulsion phase is determined based on the dielectric constant of the emulsion phase and a dielectric constant of the water phase.

7. The method of claim 1, wherein the water-in-liquid ratio of the emulsion phase is also determined based on shear rate of the emulsion phase, salinity of the emulsion phase, and continuous phase transition of the emulsion phase.

8. The method of claim 1, further comprising, prior to estimation of the thickness of the emulsion phase:
   determining the total height of the fluid as a function of an elapsed time between emitting the electromagnetic wave into the fluid and receiving a reflection of the electromagnetic wave from an interface between the water phase and a body holding the fluid; and
   determining the height of the coalescing portion of the interface between the oil phase and the emulsion phase as a function of an elapsed time between receiving a reflection of the electromagnetic wave from the coalescing portion and receiving a reflection of the electromagnetic wave from the interface between the water phase and the body holding the fluid.

9. The method of claim 1, further comprising determining kinetics of separation of the emulsion phase as a function of the thickness of the emulsion phase.

10. The method of claim 1, further comprising estimating a percentage of emulsion separation over time as a function of the thickness of the emulsion.

11. An apparatus comprising:
   a vessel containing a fluid having an oil phase, a water phase, and an emulsion phase between the oil phase and water phase;
   a guided wave radar associated with the vessel; and
   a computing device coupled to the guided wave radar and configured to:
      cause the guided wave radar to emit an electromagnetic wave into the fluid;
      measure an amplitude of a reflection of the electromagnetic wave off an interface between the oil phase and the emulsion phase, using the guided wave radar;
      determine a dielectric constant of the emulsion phase based on the amplitude of the reflection of the electromagnetic wave from the interface;
      determine a water-in-liquid ratio of the emulsion phase based on the dielectric constant;
      determine a height of a coalescing portion of the interface between the oil phase and the emulsion phase based on the emitted and reflected waves;
      determine a height of a creaming portion of the interface between the emulsion phase and the water phase based on a difference between a first product and a second product, wherein the first product comprises a product of a total height of the fluid and a total water-in-liquid ratio, and wherein the second product comprises a product of the height of a coalescing portion and the water-in-liquid ratio of the emulsion phase; and estimate a thickness of the emulsion phase from the difference between the height of the coalescing portion and the height of the creaming portion.

12. The apparatus of claim 11, wherein the vessel comprises one of a closed tank, a closed pipe, and a separator.

13. The apparatus of claim 12, wherein the vessel comprises a separator; and wherein the separator has components operable by the computing device; and wherein the computing device operates the components of the separator based on the water-in-liquid ratio or the thickness of the emulsion phase.

14. The apparatus of claim 11, further comprising a sensor associated with the vessel; and wherein the computing device is also coupled to the sensor and configured to determine the water-in-liquid ratio of the fluid based upon output from the sensor in the vessel.

15. The apparatus of claim 11, wherein the thickness of the emulsion phase is estimated using a mass balance model.

16. The apparatus of claim 11, wherein the computing device determines the dielectric constant of the emulsion phase based on the amplitude of the reflection of the electromagnetic wave from the interface and a dielectric constant of the oil phase.

17. The apparatus of claim 11, wherein the computing device determines the water-in-liquid ratio of the emulsion phase based on the dielectric constant of the emulsion phase and either a dielectric constant of the oil phase or a dielectric constant of the water phase.

18. The apparatus of claim 11, wherein the computing device determines the water-in-liquid ratio of the emulsion phase based on shear rate of the emulsion phase, salinity of the emulsion phase, and continuous phase transition of the emulsion phase.

19. The apparatus of claim 11, wherein the computing device is configured to determine the total height of the fluid as a function of an elapsed time between emitting the electromagnetic wave into the fluid and receiving a reflection of the electromagnetic wave from an interface between the water phase and a body holding the fluid; and determine the height of the coalescing portion of the interface between the oil phase and the emulsion phase as a function of an elapsed time between receiving a reflection of the electromagnetic wave from the coalescing portion and receiving a reflection of the electromagnetic wave from the interface between the water phase and the body holding the fluid.

* * * * *